(12) United States Patent
Hart et al.

(10) Patent No.: US 9,579,180 B2
(45) Date of Patent: Feb. 28, 2017

(54) METHOD OF TREATING PELVIC PROLAPSE USING A SACROCOLPOPEXY/SACROCERVICOPEXY VAGINAL POSITIONING AND MESH RETENTION SYSTEM

(71) Applicants: Stuart Richard Hart, Tampa, FL (US); Mario Alves Simoes, Pinellas Park, FL (US); Mark Evans Armstrong, Tampa, FL (US); Omar Carambot, Orlando, FL (US)

(72) Inventors: Stuart Richard Hart, Tampa, FL (US); Mario Alves Simoes, Pinellas Park, FL (US); Mark Evans Armstrong, Tampa, FL (US); Omar Carambot, Orlando, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 15/211,723

(22) Filed: Jul. 15, 2016

(65) Prior Publication Data

US 2016/0317271 A1    Nov. 3, 2016

Related U.S. Application Data

(62) Division of application No. 14/755,666, filed on Jun. 30, 2015, now Pat. No. 9,414,904.

(60) Provisional application No. 62/018,738, filed on Jun. 30, 2014.

(51) Int. Cl.
*A61F 2/00* (2006.01)
*A61M 25/10* (2013.01)

(52) U.S. Cl.
CPC .......... *A61F 2/0045* (2013.01); *A61F 2/0063* (2013.01); *A61M 25/10* (2013.01)

(58) Field of Classification Search
CPC ............................ A61B 17/42; A61B 17/0218
USPC .................................................. 600/37, 29–31
See application file for complete search history.

(56) References Cited

U.S. PATENT DOCUMENTS

| | | | | |
|---|---|---|---|---|
| 5,840,077 A | * | 11/1998 | Rowden | A61B 17/4241 606/119 |
| 8,292,901 B2 | * | 10/2012 | Auerbach | A61B 17/4241 600/185 |
| 2012/0016185 A1 | * | 1/2012 | Sherts | A61B 17/12099 600/37 |
| 2014/0074051 A1 | | 3/2014 | Berman et al. | |
| 2015/0105792 A1 | * | 4/2015 | Adams | A61B 17/42 606/119 |

(Continued)

OTHER PUBLICATIONS

Carey M. et al., Vaginal surgery for pelvic organ prolapse using mesh and a vaginal support device, BJOG, 2008, 115 (3):391-397.

(Continued)

*Primary Examiner* — Samuel Gilbert
(74) *Attorney, Agent, or Firm* — Michele L. Lawson; Smith & Hopen, P.A.

(57) ABSTRACT

A method of treating pelvic prolapse is presented herein. Vaginal support device contains flat superior and inferior surfaces to facilitate affixing of mesh to vagina. Vaginal support device may be used as part of a system in conjunction with a manipulation device to support the vaginal walls. Mesh retention system may also include a holding device and retention mechanism such as a catheter or shaft and corresponding catheter balloon to hold mesh in place.

7 Claims, 8 Drawing Sheets

(56) References Cited

U.S. PATENT DOCUMENTS

2015/0164553 A1   6/2015  Dolan et al.

OTHER PUBLICATIONS

Rosati, M. et al., Efficacy of Laparoscopic Sarcocervicopexy for Apical Support of Pelvic Organ Prolapse, J Soc Laparoendoscopic Surgeons, 2013, 17(2):235-244.

* cited by examiner

METHOD OF TREATING PELVIC PROLAPSE USING A SACROCOLPOPEXY/SACROCERVICOPEXY VAGINAL POSITIONING AND MESH RETENTION SYSTEM

CROSS REFERENCE TO RELATED APPLICATIONS

This application is a divisional of and claims priority to U.S. patent application Ser. No. 14/755,666, entitled "Sacrocolpopexy/Sacrocervicopexy Vaginal Positioning and Mesh Retention System", filed Jun. 30, 2015, which is a nonprovisional of and claims priority to U.S. Provisional Patent Application No. 62/018,738, entitled "Sacrocolpopexy/Sacrocervicopexy Vaginal Positioning and Mesh Retention System", filed Jun. 30, 2014, the entire contents of each of which is herein incorporated into this disclosure.

FIELD OF INVENTION

This invention relates to devices, systems and procedures to treat pelvic organ prolapse. Specifically, the invention describes a vaginal support device, system and associated method of treating prolapse using a sacrocolpopexy/sacrocervicopexy vaginal positioning and mesh retention system.

BACKGROUND OF THE INVENTION

Vaginal prolapse occurs when the bladder, uterus and/or bowel protrude into the vagina, typically due to loss of natural support for the pelvic organs and the vaginal vault. Vaginal prolapse occurs most often in women who have undergone a prior hysterectomy, however prolapse may also occur in women who still have a uterus.

In the normal female anatomy, direct support for the vaginal vault is provided by the parametrium (cardinal and uterosacral ligaments) and paracolpium fibers. These fibers act like suspensory ligaments and arise from the fascia of the piriformis muscle, sacroiliac joint and lateral sacrum. The fibers insert into the lateral upper third of the vagina. Indirect support for the vaginal vault is provided by the levator plate, formed by the fusion of the right and left levator ani muscles located between the rectum and coccyx. Pelvic organ prolapse and vaginal vault prolapse occurs after failure of these direct and indirect supporting mechanisms and is frequently accompanied by weakness of the muscular pelvic floor and suspensory fibers of the parametrium and upper paracolpium.

It has been reported that each year in the USA, approximately 200,000 women undergo surgery for pelvic organ prolapse and that 11.1% of women had undergone surgery for pelvic organ prolapse, urinary incontinence or both by age 80. Repeat surgery for recurrent prolapse was required in 29.2% within 4 years of the primary surgical procedure. Women less than 60 years of age and women with higher grades of prolapse seem to be more likely to experience recurrent prolapse after vaginal repair surgery. (Carey M. et al., Vaginal surgery for pelvic organ prolapse using mesh and a vaginal support device, *BJOG*, 2008, 115(3):391-397)

Pelvic organ prolapse is the symptomatic descent of one or more of components of the vaginal wall, including the anterior wall, posterior wall, and the vaginal apex, which could lead to descent of the cervix and uterus or the vaginal cuff following a hysterectomy. Nomenclature exists to describe the prolapse based on the pelvic organ that has herniated into the vaginal wall. Anterior defects with herniation of the urinary bladder into the vagina creates a cystocele. A retocele occurs from posterior vaginal wall defects, particularly from the rectum bulging into the vagina. A hysterocele occurs when the uterus descends into the vagina thus resulting in a vaginal vault descent. Apical defects include uterine prolapse or uterovaginal prolapse, vaginal cuff prolapse after hysterectomy, and enteroceles. An enterocele is protrusion of the intestines into the apical vaginal wall and can be in either the anterior or posterior compartment.

There are a variety of surgical techniques that may be used to repair pelvic organ prolapse, including vaginal, abdominal and laparoscopic approaches, with each approach having advantages and disadvantages in light of the others.

Sacrocolpopexy is a surgical technique for repairing pelvic organ prolapse, specifically apical or vaginal vault prolapse in women. Vaginal vault prolapse may occur in women who have had a hysterectomy. Vaginal vault prolapse occurs when the vagina descends from its normal position, sometimes out through the vaginal opening. Sacrocolpopexy is generally performed on women who have had a hysterectomy and thus the uterus and cervix are removed.

Generally, reconstruction is accomplished through open abdominal surgery or through minimally invasive surgery such as laparoscopy or robotic-assisted techniques. The technique involves suspending the vaginal apex to the sacral promontory so as to recreate the natural anatomic support that is normally provided by the uterosacral and cardinal ligaments. In treating vaginal vault prolapse, support of the pelvic organs is generally achieved by attaching a piece of material, such as mesh, usually from the top and back of the vagina to a ligament of the lower backbone. Mesh may be attached to the apex of the vagina as well as to the anterior and/or posterior wall.

Abdominal sacrocolpopexy is associated with a lower rate of recurrent vault prolapse, reduced grade of residual prolapse, longer time to recurrence, and less dyspareunia compared with the vaginal procedures, such as sacrospinous ligament fixation and uterosacral ligament suspension. (Rosati, M. et al., Efficacy of Laparoscopic Sarcocervicopexy for Apical Support of Pelvic Organ Prolapse, *J Soc Laparoendoscopic Surgeons*, 2013, 17(2):235-244)

Laparoscopic sacrocolpopexy aims to bridge the gap between the abdominal and vaginal procedures to provide the best outcomes of abdominal sacrocolpopexy with decreased morbidity similar to vaginal procedures. Although sacrocolpopexy, which is performed by interposing a synthetic mesh between the vaginal cuff and the bone, is effective, it is associated with a mesh erosion rate between 0.8% and 9%. (Rosati 2013)

Sacrocervicopexy is a procedure similar to sacrocolpopexy, in which a graft material is used to suspend the cervix to the anterior longitudinal ligament of the sacrum. The technique is normally performed laparoscopically by attaching synthetic mesh to the front and back of the vagina and subsequently to the sacrum. It has generally been used to treat uterovaginal prolapse in women having a cervix and desiring to preserve their uterus and fertility. Sacrocervicopexy can be performed either with uterine preservation or after supracervical hysterectomy and may avoid the risk of mesh erosion while preserving the integrity of the uterosacral and cardinal ligaments, which are the main supports of the vaginal apex. It may be associated with vaginal surgery (colporraphy) in all cases of concomitant anterior or posterior prolapse. (Rosati 2013)

Prior art devices have generally been vaginal stents/support devices that resemble a solid rounded cylinder-like device. These vaginal support devices having a rounded surface made it very difficult to affix the mesh to the vagina.

What is needed is a vaginal support device and system capable of providing a flat surface for affixing the mesh and facilitating the placement and affixing of mesh to treat pelvic organ prolapse.

SUMMARY OF INVENTION

The inventors have developed a novel device, system and associated method of treating prolapse using a sacrocolpopexy/sacrocervicopexy vaginal positioning and mesh retention system.

In an embodiment, a vaginal support device is presented comprising: a hollow body having anterior and posterior portions, superior and inferior surfaces, two opposing sides and proximal and distal ends; an aperture positioned in the distal end of the anterior portion of the hollow body; and an orifice positioned in the proximal end of the posterior portion of the hollow body. The distal end of the anterior portion may be rounded and the two opposing sides may be slightly convex so as to facilitate insertion of the device into the vagina.

The superior and inferior surfaces may be flat and taper towards each other from the proximal end to the distal end so as to provide a flat sloped surface. The thickness of the body between the superior and the inferior surfaces of the posterior portion defines a posterior height while the thickness of the body between the superior and the inferior surfaces of the anterior portion defines an anterior height. In general, the posterior height is greater than the anterior height.

The device may also include attachment means positioned on the proximal end of the posterior portion of the hollow body.

A system for treating pelvic prolapse is also presented comprising: a vaginal support device having attachment means positioned on the proximal end of the posterior portion of the hollow body of the vaginal support device, as previously described, attached to a manipulation device by the attachment means. The manipulation device is used to position the system in the pelvic region.

The system also may include a holding device extending through vaginal support device so that distal tip of holding device protrudes from the aperture as well as retention means positioned at the protruding distal tip of holding device. In an embodiment, the retention means may be a catheter balloon.

A method of treating pelvic prolapse is presented comprising: attaching a vaginal support device to a manipulation device to form a system as described above; inserting a holding device into manipulation device wherein the holding device extends through the orifice and the aperture in the vaginal support device; inserting the vaginal support device into vagina; inserting the holding device through the vaginal cuff or the cervical os so that the distal tip of the holding device is visible inside pelvis when viewing laparoscopically; positioning a surgical mesh over tip of the holding device which is protruding through the aperture; positioning the system so that the mesh is adjacent to area of interest; deploying a retention mechanism to hold the surgical mesh against the vagina; affixing the mesh to the vagina or the cervix and longitudinal ligament of the sacrum; and retracting the system from the vagina.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

DEFINITIONS

"Flat" as used herein refers to a smooth and even surface without marked lumps or indentations. The term "flat" as used herein with respect to the superior and inferior surfaces does not necessarily indicate that the surface is horizontal or level, but rather only that it is smooth. In some embodiments, superior and inferior surfaces may be horizontal/level while in other embodiments the surfaces are sloped.

"System" as used herein refers to the combination of the vaginal support device with a manipulation device for use in sacrocolpopexy and sacrocervicopexy procedures to treat pelvic organ prolapse. The system may also include a holding device and retention mechanism to hold the mesh in place.

"Slightly" as used herein refers to a small degree or amount. With regard to the embodiment in which the sides are described as being slightly convex, it is meant to convey that the sides are curving or extending outward a small amount.

"Convex" as used herein refers to a shape or surface which is curved outwardly. Many shapes are contemplated including, but not limited to, hyperbolic, elliptical, circular, etc.

As described above, pelvic organ prolapse is the symptomatic descent of one or more of components of the vaginal wall, including the anterior wall, posterior wall, and the vaginal apex, which could lead to descent of the cervix and uterus or the vaginal cuff following a hysterectomy. Sacrocolpopexy and sacrocervicopexy is a procedure to treat pelvic organ prolapse and has become the gold standard surgical procedure in many cases for significant prolapse.

Figure 1:
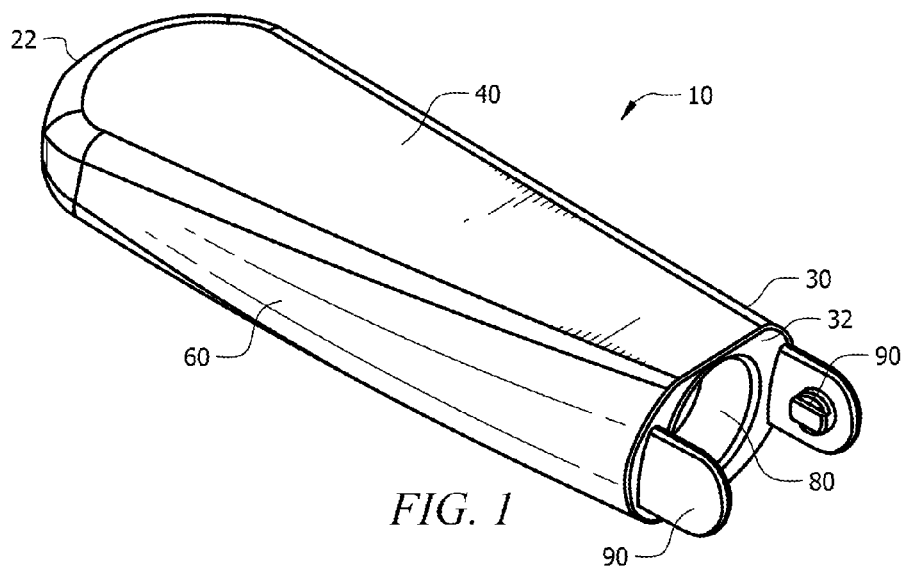
FIG. 1 is a perspective view of the vaginal support device.
Figure 2:
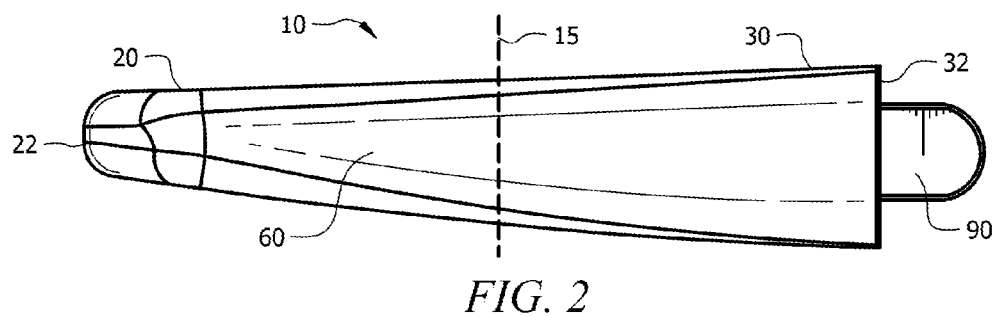
FIG. 2 is a side view of the vaginal support device.
Figure 3:
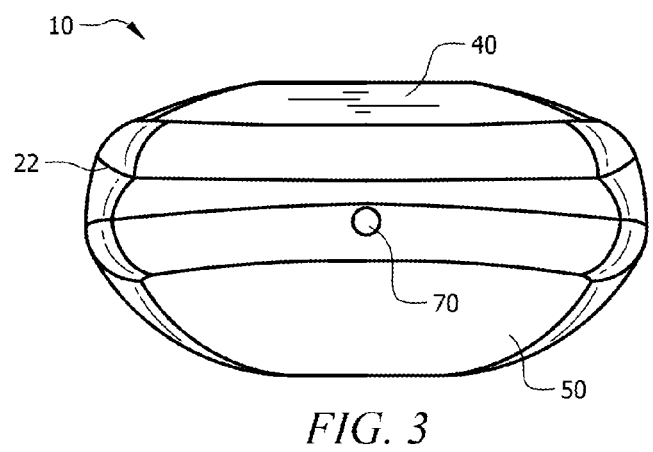
FIG. 3 is a front view of the top of the vaginal support device.
Figure 4:
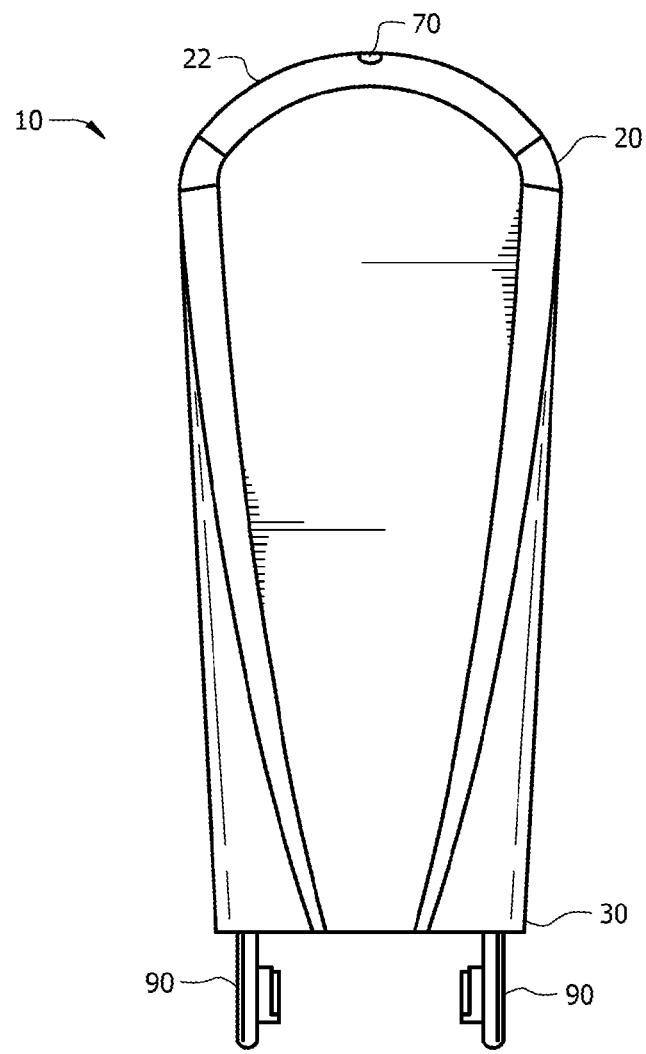
FIG. 4 is a top view of the vaginal support device.
Figure 5:
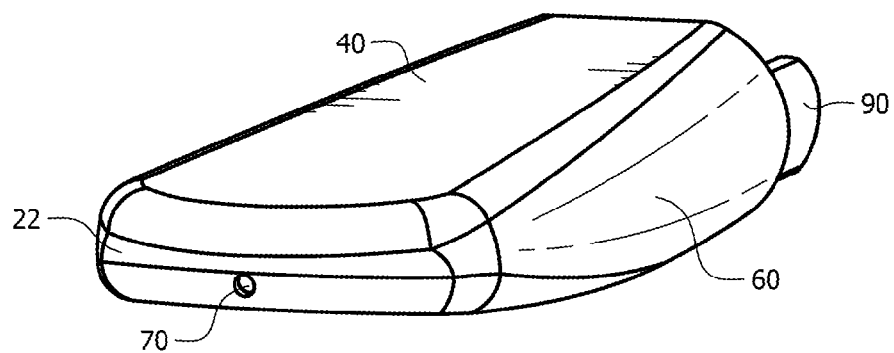
FIG. 5 is a top perspective view of the vaginal support device.
Figure 6:
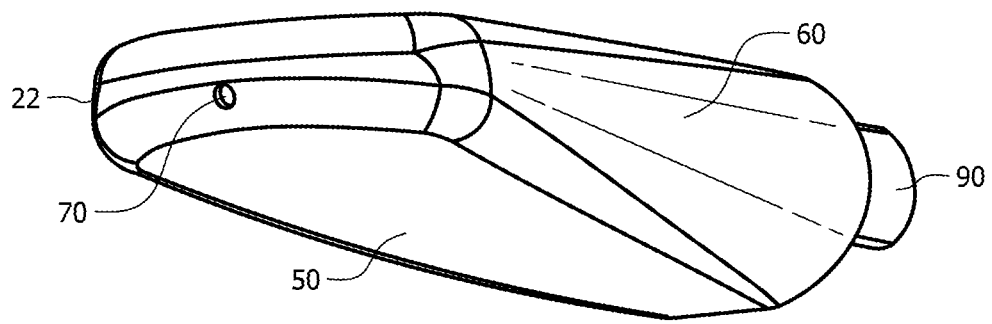
FIG. 6 is a bottom perspective view of the vaginal support device.
Figure 7:
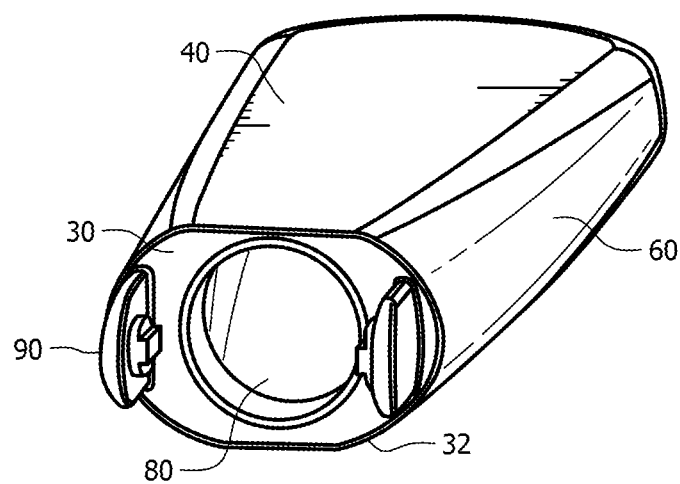
FIG. 7 is perspective view of the bottom of the vaginal support device.
Figure 8:
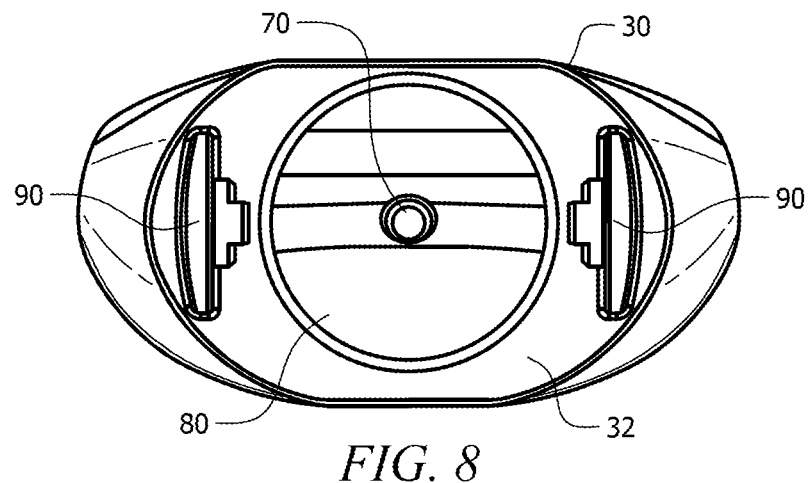
FIG. 8 is a bottom view of the bottom of the vaginal support device.
Figure 9:
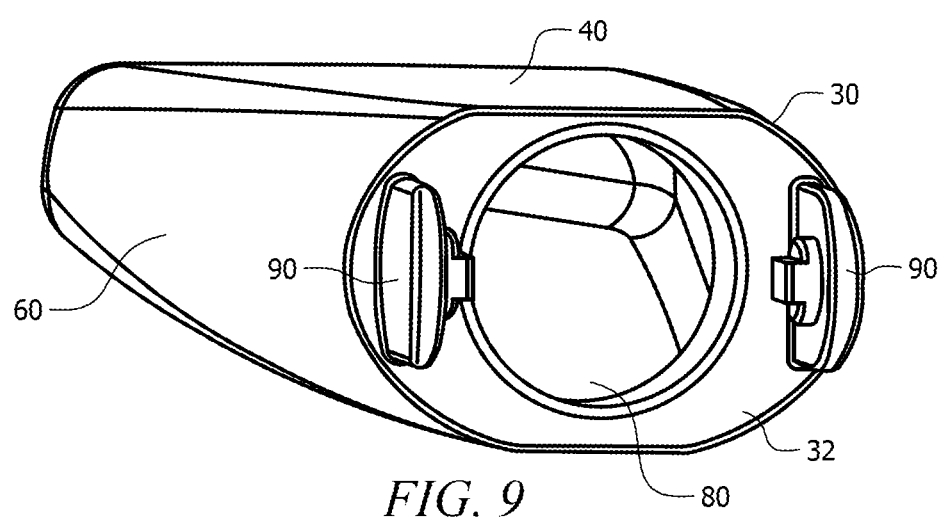
FIG. 9 is a perspective view of the bottom of the vaginal support device.
Figure 10:
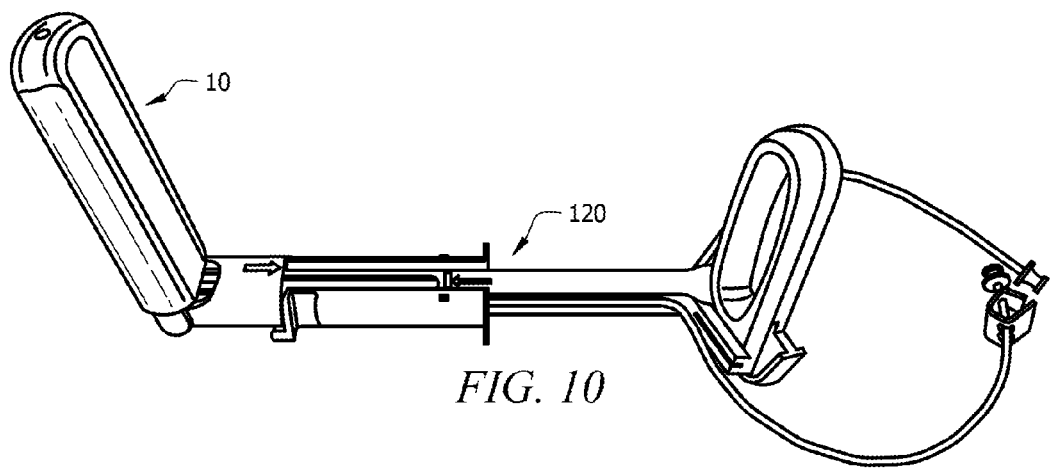
FIG. 10 is a side perspective view of the vaginal support device attached to a manipulation device. The manipulation device shown is the Cooper RUMI® uterine positioning system.
Figure 11:
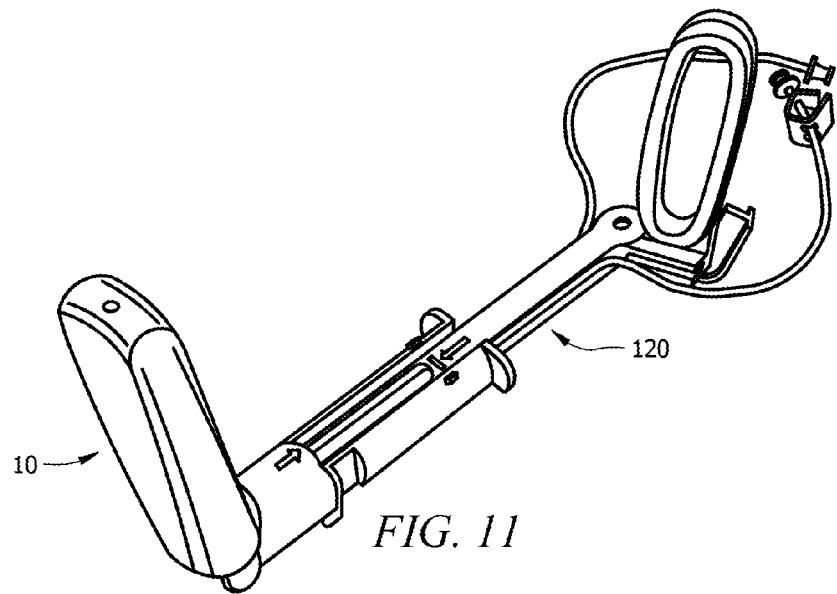
FIG. 11 is a perspective view of the vaginal support device attached to a manipulation device. The manipulation device shown is the Cooper RUMI® uterine positioning system.
Figure 12:
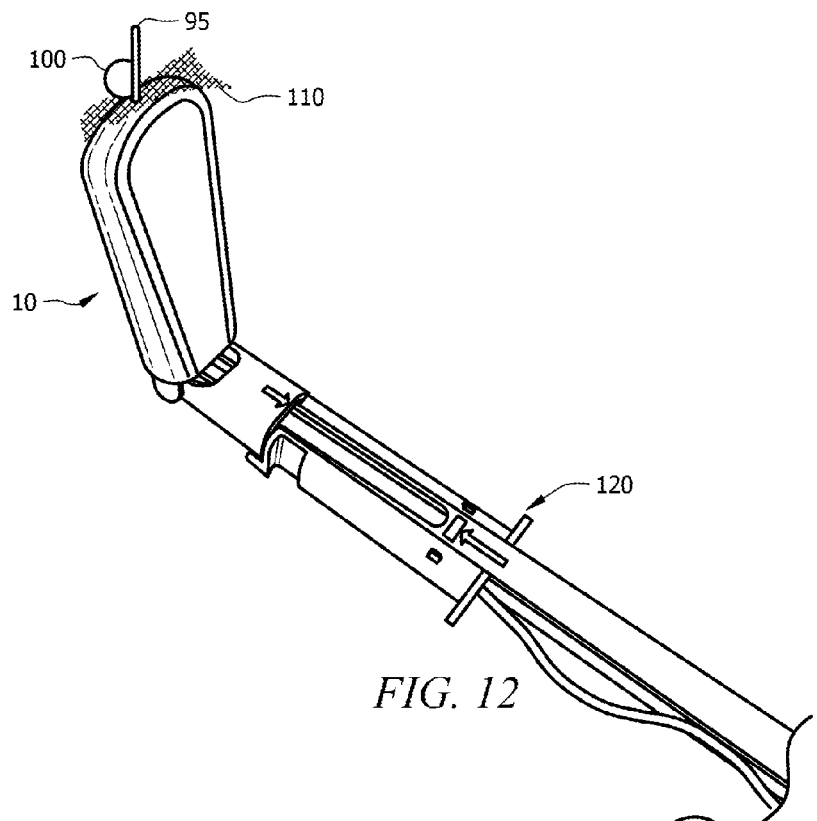
FIG. 12 is a side perspective view of the vaginal support device attached to a manipulation device. The manipulation device shown is the Cooper RUMI® uterine positioning system. The image illustrates the mesh being attached to the tip of the shaft and being held in place by a catheter balloon as the retention mechanism.
Figure 13:
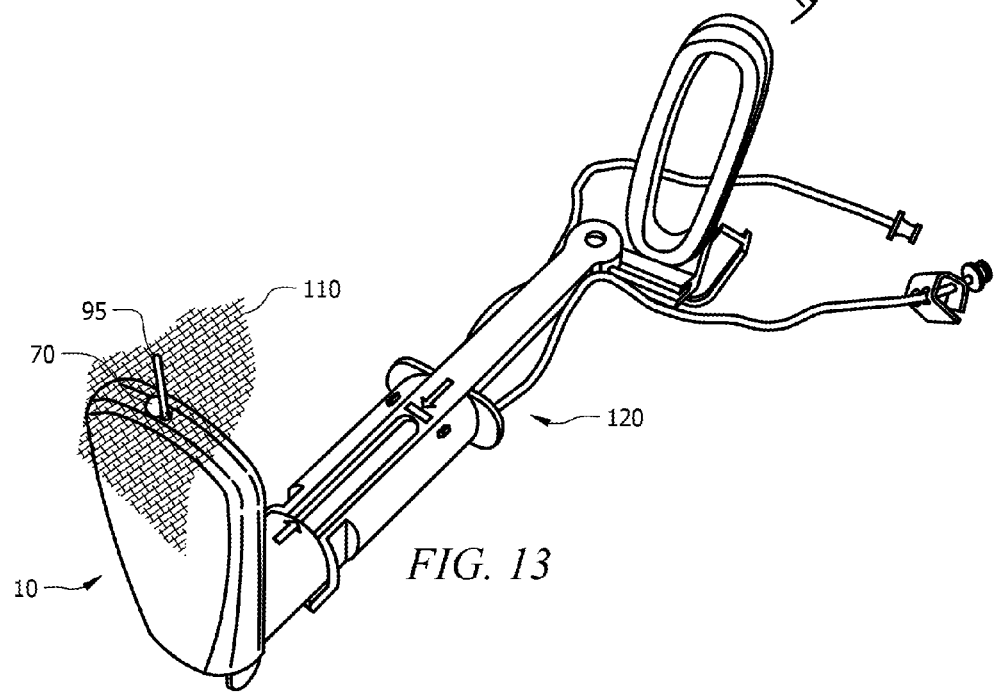
FIG. 13 is a front perspective view of the vaginal support device attached to a manipulation device. The manipulation device shown is the Cooper RUMI® uterine positioning system. The image illustrates that the tip of the shaft is threaded through a pore in the surgical mesh.
Figure 14:
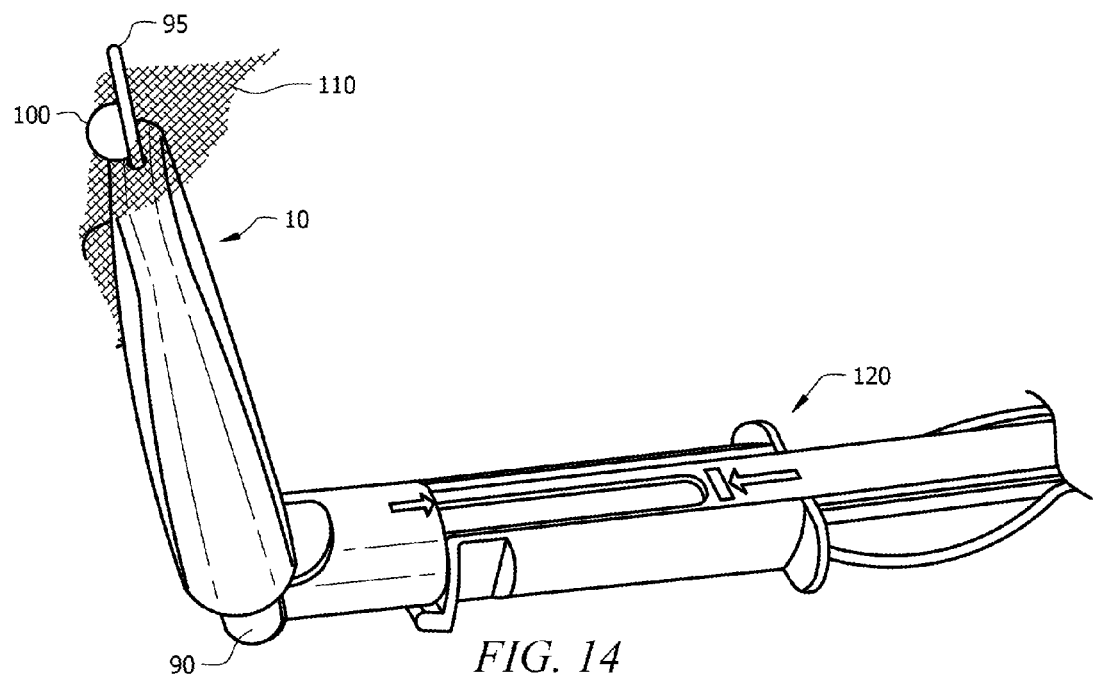
FIG. 14 is a perspective view of the vaginal support device attached to a manipulation device. The manipulation device shown is the Cooper RUMI® uterine positioning system. The surgical mesh is shown as being held in place by a catheter balloon.
Figure 15:
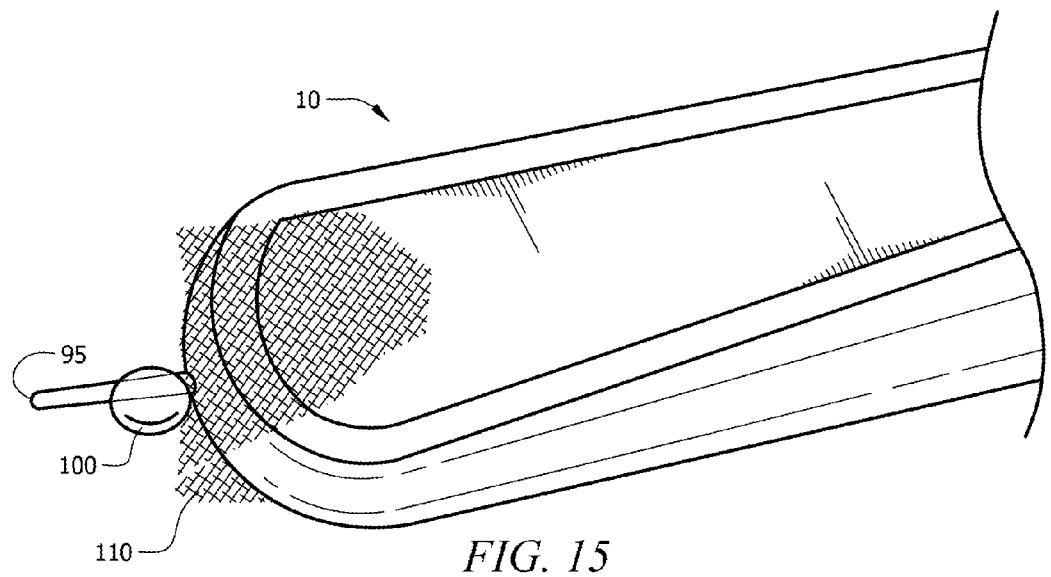
FIG. 15 is a top view of the vaginal support device attached to a manipulation device. The manipulation device shown is the Cooper RUMI® uterine positioning system. The surgical mesh is shown as being held in place by a catheter balloon.
Figure 16:
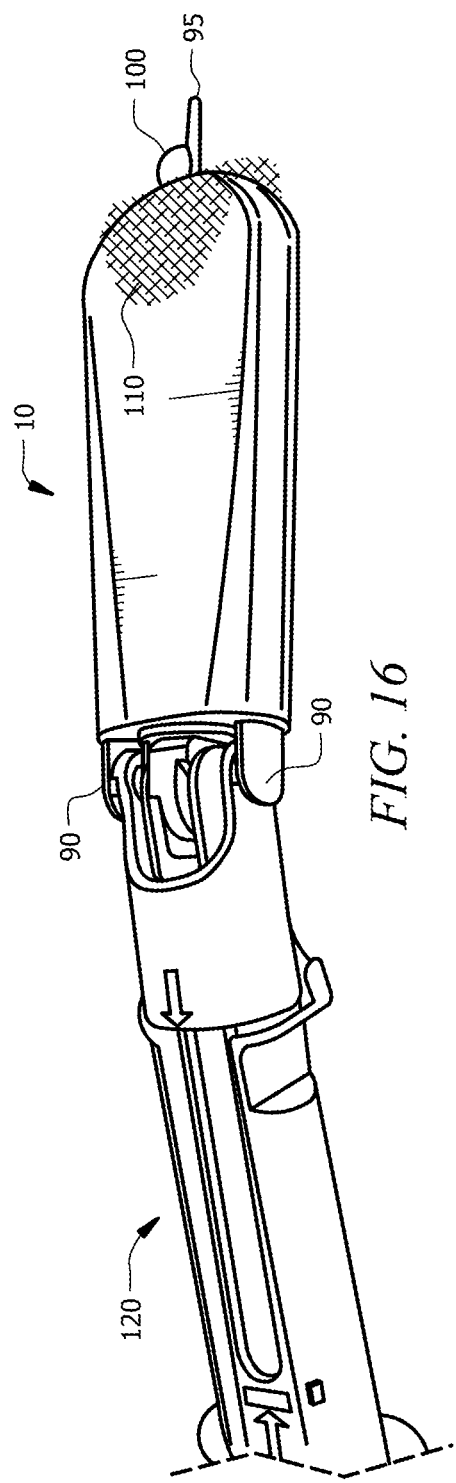
FIG. 16 is a bottom view of the vaginal support device attached to the Cooper RUMI® uterine positioning system.

In an embodiment, the invention includes an ergonomically shaped internal vaginal support to facilitate the suturing of mesh to the anterior and posterior aspects of the vagina during sacrocolpopexy and sacrocervicopexy surgical procedures. Vaginal support device 10 may be comprised of a hollow body having anterior 20 and posterior 30 portions, superior 40 and inferior 50 surfaces and a pair of opposing sides 60. (FIGS. 1-9) As depicted in FIG. 2, transverse plane 15 defines an artificial boundary between anterior 20 and posterior 30 portions of device.

In an embodiment, vaginal support device 10 may be substantially trapezoidal in shape having distal end 22 that is slightly wider than proximal end 32. In other embodiments, vaginal support device 10 is of essentially the same width from distal 22 to proximal end 32 resembling a rectangular shape.

Distal end 22 of anterior portion 20 of device 10 is rounded along its perimeter so as to facilitate insertion into the vagina. Alternatively, distal end 22 of anterior portion 20 of vaginal support device may be rounded only along the corner edges. Distal end 22 of anterior portion 20 contains aperture 70 through which holding device 95 and retention mechanism 100 may pass. In some embodiments, aperture 70 is positioned substantially centrally in distal end 22 of anterior portion 20. Aperture 70 is sized accordingly to allow holding device 95 and retention mechanism 100 to extend therethrough.

Holding device 95 may include any means capable of holding mesh 110 including, but not limited to, a shaft or catheter; a coil that may be advanced through a piece of mesh by a screw-type mechanism; and a spring-loaded grasping tip. In some embodiments, holding device 95 is a flexible shaft/catheter that can be bent to 90 degrees or greater. In other embodiments, holding device 95 is rigid.

Retention mechanism 100 may include any retention means capable of holding a piece of mesh known in the art including, but not limited to, a catheter balloon mechanism; a rigid metallic or plastic arm that can be deployed and retracted from holding device 95; and a multiple pronged mechanism deployed from the interior of the shaft. If a catheter balloon mechanism is used, the balloon tip is inflated once positioned through the mesh to hold the mesh in place while being sutured. Once the mesh is sutured to the tissue, the balloon tip may be deflated and the catheter balloon mechanism removed.

Proximal end 32 of posterior portion 30 contains orifice 80 through which a portion of manipulation device 120 is inserted to attach vaginal support device 10 to manipulation device 120. At least one attachment means 90 is positioned on proximal end 32 of posterior portion 30 to attach vaginal support device 10 to manipulation device 120. (FIGS. 1, 4 and 7-9) Attachment means 90 includes any means known in the art capable of attaching vaginal support device 10 to manipulation device 120 including, but not limited to, male and female adapters, screws, bolts, prongs, latches, threaded adapters, grooved adapters, etc. In an embodiment, attachment means 90 may be a pair of prongs adapted to attach vaginal support device 10 to distal end of manipulation device 120.

Superior 40 and inferior 50 surfaces of device 10 are substantially flat so as to provide a smooth surface for suturing of mesh both anteriorly and posteriorly. In an embodiment, superior 40 and inferior 50 surfaces taper inward from proximal end 32 of posterior portion 30 to distal end 22 of anterior portion 20 thus creating a slight slope between superior 40 and inferior 50 surfaces of device. The height between superior 40 and inferior 50 surfaces in posterior portion 30 defines a posterior height. The height between superior 40 and inferior 50 surfaces in anterior portion 20 defines an anterior height. Posterior height is larger than anterior height as depicted in FIG. 2.

In an alternative embodiment, superior 40 and inferior 50 surfaces may not taper in which case, anterior and posterior height are essentially equal.

Superior 40 and inferior 50 surfaces are connected to each other by a pair of opposing sides 60. Sides 60 may be slightly curved or rounded in a convex manner to provide a rounded shape to device 10 to facilitate insertion into the vagina. In an alternative embodiment, sides may be substantially straight having only rounded edges where superior 40 and inferior 50 surfaces meet sides 60.

Vaginal support device 10 may be used as an attachment to manipulation device 120 such as the Cooper RUMI® uterine positioning system. The term "system" refers to the combination of vaginal support device 10 with manipulation device 120. The system may also include holding device 95 and retention mechanism 100 which holds the surgical mesh to the intraabdominal aspect of the vaginal cuff or the remaining portion of the cervix after supracervical hysterectomy, respectively. Manipulation device 120 is used to position vaginal support device 10 within the vagina. Manipulation device 120 preferably is comprised of a handle as well as corresponding attachment means for attaching vaginal support device 10 to distal end. Manipulation device 120 also may include a catheter management system to allow for control over inflation/deflation of catheter balloon as well as advancement/retraction of catheter.

FIGS. 10-16 illustrate vaginal support device 10 attached to manipulation device 120. The Cooper RUMI® uterine positioning device is shown in the images, however any manipulation device capable of attaching to vaginal support device 10 may be used as long as the manipulation device has attachment means to attach the vaginal support device to it. The manipulation device must also be capable of being held in a rigidly fixed position to ensure there is no movement of the manipulation device. In an embodiment, the manipulation device can be non-jointed adapter. As shown in FIGS. 12-16, surgical mesh may be held in place on anterior portion 20 of vaginal support device 10 by holding device 95 and retention mechanism 100. A shaft/catheter and catheter balloon are illustrated in the figures as exemplary holding devices and retention mechanisms, however other holding devices and retention mechanisms are contemplated as described previously. Once retained, surgical mesh 110 is able to be affixed to the vagina.

The Cooper RUMI® handle is a manipulation system comprised of a reusable handle that can be used in laparoscopic pelvic surgery. The handle is usable with various sized tips having a silicone balloon. In use, holding device 95 with retention mechanism 100 is passed through manipulation system 120 and inserted through orifice 80 and continues through aperture 70 in device 10. Holding device 95 may have mesh 110 attached at its distal end. Mesh 110 can be held in place through holding device 95 and retention mechanism 100 such as an inflatable balloon on catheter. While device 10 is described as usable in a system with the Cooper RUMI® handle, any manipulation system which permits the attachment of device 10 and passage of a catheter or shaft through device 10 so that mesh 110 can be used to treat pelvic organ prolapse, is contemplated by the invention, as described previously.

In use, vaginal support device 10 is attached to manipulation device 120 and the entire system, with the exception of the handle of manipulation device 120, is inserted into the vaginal cavity with holding device 95 being positioned through either the cervical os or the center of the vaginal cuff. Surgical mesh 110 is positioned over holding device 95 by threading holding device 95 through a pore in mesh 110. After mesh 110 is positioned on the tissue, retention mechanism 100, such as a catheter balloon, is deployed to hold surgical mesh 110 to the cervical or vaginal tissue. Surgical mesh 110 is then sutured to the vaginal walls anteriorly and posteriorly, as well as the longitudinal ligament of the sacrum. The suturing of the surgical mesh can be accomplished using laparoscopic tools as in a sacrocolpopexy or sacrocervicopexy procedure.

In some embodiments, holding device 95 is inserted through either the cervical os or the center of the vaginal cuff prior to the entire system being inserted into the vagina. In this embodiment, holding device 95, such as a catheter or rod, can be threaded through support device 10 prior to insertion into the vagina. Holding device 95 can be threaded through the cervical os or through the vaginal cuff, under laparoscopic visualization, with support device 10 inserted by sliding support device 10 over holding device 95 proximally to distally until support device 10 is positioned within the vagina.

The instant invention addresses several surgical issues encountered during sacrocolpopexy/sacrocervicopexy surgeries. The shape of the vaginal support provides the surgeon with flat surfaces on which to suture the mesh both anteriorly and posteriorly. Also, due to its attachment to the RUMI uterine positioning system or any other proprietary manipulation system, the device can be angled to expose the posterior aspect of the vagina for suturing of mesh, which is generally a very difficult task to perform with laparoscopic instrumentation due to its anatomical location. Additionally, the rigid shaft/catheter mesh retention mechanism keeps the surgical mesh from slipping out of position during movement of the vagina.

The vaginal support device may be provided in a variety of sizes to accommodate the anatomical features of different women treated using the device. Size variation may occur with respect to length, transverse width and/or height of the device.

The vaginal support device may be made from a variety of materials including, but not limited to, medical grade silicone, plastic, PVC, etc. The materials for manufacture are preferably bio-compatible so as to not cause injury to the patient. The vaginal support device is preferably made of a rigid material to allow the device to provide support within the vagina for affixation of the mesh.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of treating pelvic prolapse comprising:
   attaching a vaginal support device to a separate manipulation device to form a system wherein the vaginal support device is comprised of
   a rectangular wedge-shaped hollow body having anterior and posterior portions, superior and inferior surfaces, two slightly convex opposing sides and proximal and distal ends;
   an aperture positioned in the distal end of the anterior portion of the rectangular wedge-shaped hollow body;
   an orifice positioned in the proximal end of the posterior portion of the rectangular wedge-shaped hollow body; and
   attachment means positioned on the proximal end of the posterior portion of the rectangular wedge-shaped hollow body for attachment to the separate detachable manipulation device;
   wherein the anterior and posterior portions of the rectangular wedge-shaped hollow body are substantially equal in length and the anterior portion being wider than the posterior portion of the rectangular wedge-shaped hollow body;
   wherein each of the two opposing sides form a single solid continuous surface;
   wherein the superior and inferior surfaces extend to the distal end of the device and taper towards each other from the proximal end to the distal end so as to provide a sloped surface;
   wherein the distal end of the anterior portion is rounded;
   wherein both the aperture and the orifice are of sufficient size to allow insertion of a holding device;
   inserting the holding device into the separate manipulation device wherein the holding device extends through the orifice and the aperture in the vaginal support device;
   inserting the vaginal support device into vagina;
   inserting the holding device through vaginal cuff or cervical os wherein distal tip of the holding device is visible inside pelvis when viewed through vaginal opening;
   positioning a surgical mesh over the distal tip of the holding device which is protruding through the aperture;

positioning the system so that the mesh is adjacent to area of interest;

deploying a retention mechanism to hold the surgical mesh against the vagina or a cervix;

affixing the mesh to the vagina or the cervix and longitudinal ligament of sacrum; and retracting the system from the vagina.

2. The method of claim 1, wherein the retention mechanism is a catheter balloon.

3. The method of claim 1, wherein the attachment means are selected from the group consisting of prongs, male and female adapters, screws, bolts, latches, threaded adapters, and grooved adapters.

4. The method of claim 1, wherein thickness of the body between the superior and the inferior surfaces of the posterior portion define a posterior height.

5. The method of claim 4, wherein thickness of the body between the superior and the inferior surfaces of the anterior portion define an anterior height.

6. The method of claim 5, wherein the posterior height is greater than the anterior height.

7. The method of claim 1, wherein the attachment means are a pair of prongs wherein one prong is positioned on each of the opposing sides with the orifice located between the pair of prongs.

* * * * *